United States Patent [19]

Castellini

[11] Patent Number: 5,167,501
[45] Date of Patent: Dec. 1, 1992

[54] TOOL HEAD FOR DENTISTRY HANDPIECES AND THE METHOD OF EMBODYING SUCH A HEAD

[75] Inventor: Franco Castellini, Bologna, Italy
[73] Assignee: Castellini, SPA, Bologna, Italy
[21] Appl. No.: 868,480
[22] Filed: Apr. 14, 1992
[30] Foreign Application Priority Data
  Apr. 30, 1991 [IT] Italy .................... B091A 000144
[51] Int. Cl.$^5$ .................................................. A61C 1/12
[52] U.S. Cl. ........................................ 433/82; 433/132
[58] Field of Search ............................... 433/82, 132
[56] References Cited
U.S. PATENT DOCUMENTS

| | | | |
|---|---|---|---|
| 3,256,604 | 6/1966 | Borden | 433/82 |
| 3,451,134 | 6/1969 | Erickson et al. | 433/82 |
| 3,783,515 | 1/1974 | Auphan et al. | 433/82 |
| 3,952,416 | 4/1976 | Lingenhole | 433/82 |
| 5,078,601 | 1/1992 | Badoz et al. | 433/82 |

FOREIGN PATENT DOCUMENTS

| | | | |
|---|---|---|---|
| 0109507 | 5/1984 | European Pat. Off. | 433/82 |
| 0236820 | 9/1987 | European Pat. Off. | 433/82 |

*Primary Examiner*—John J. Wilson
*Attorney, Agent, or Firm*—Laff, Whitesel, Conte & Saret

[57] ABSTRACT

A typical turbine handpiece comprises a housing accommodating the air-driven rotor, and in the head disclosed, the base of this housing is extended to create an annular seating connected at bottom with the water line of the spray circuit and occupied by a first ring exhibiting an annular cavity connected by way of a lateral orifice to the spray air line. A portion of the ring not occupied by the cavity is shaped so as to fill the annular seating only in part, thereby creating a gap admitting water from the spray circuit; the ring also affords a set of through holes connecting the cavity both with the gap and with a corresponding set of angled outlet holes in the bottom part of the head, from which sprays are directed convergently onto the tip of the bur. The seating and the cavity are enclosed by a second ring inserted from the turbine side to a fluid-tight fit.

6 Claims, 2 Drawing Sheets

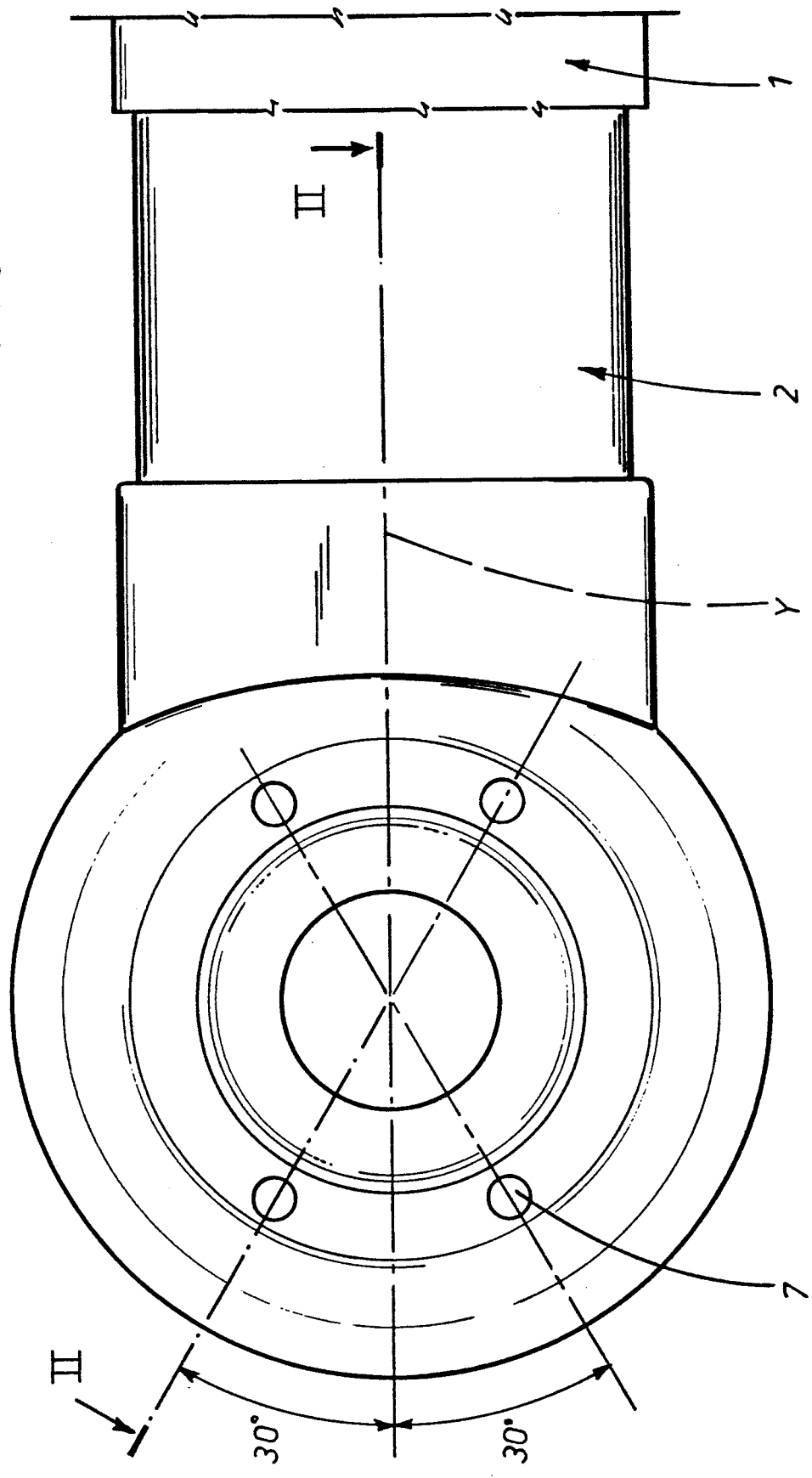

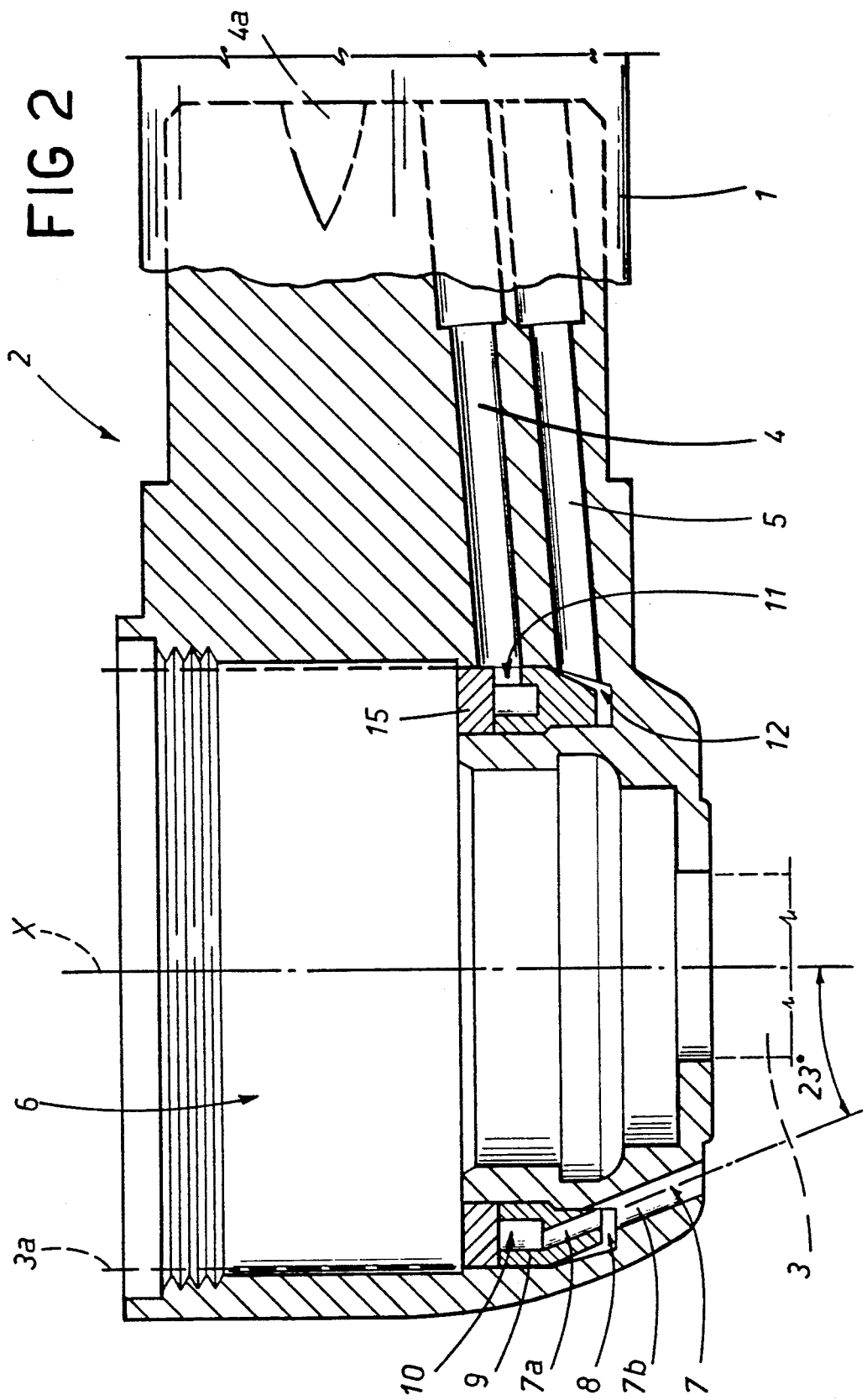

TOOL HEAD FOR DENTISTRY HANDPIECES AND THE METHOD OF EMBODYING SUCH A HEAD

BACKGROUND of the INVENTION

The present invention relates to a tool head, in particular for dentistry instruments or handpieces, and to the method of embodying such a head.

In the art field of dental surgery, use is made in particular of turbine handpieces comprising a grip of which one end carries a head serving to support and retain a bur, the actual tool which is inserted by the surgeon into the oral cavity of the patient. The rear end of the handpiece is connected to fluid lines carrying pressurized air and water, which are directed along the length of the grip and emerge at the head; the air serves to rotate the turbine, and in addition, a mixture of air and water is sprayed from a set of holes converging on the tip of the bur, cooling the cutting edges and the treatment area and functioning also as a cleansing agent. The head itself is of circular section, and affords a housing at the side remote from the bur in which the turbine or rotor is stably accommodated, whilst the bur side incorporates a small annular seating designed to hold a coaxially disposed metal insert, likewise annular, retained in a fluid-tight fit; this same insert (e.g. as disclosed in EP 236 820) constitutes a working part of the head from which the spray of cooling fluid is released, and to that end is embodied with outlet holes and connected to internal passages carrying the air and the water through the handpiece.

In assembly, the insert and the head are united by a force fit in conjunction with sealing means, an arrangement which is a source of problems regarding the structural architecture of the head as a whole; in effect, the addition of the insert increases the axial dimension of the head, a factor occasioning practical difficulties when maneuvering in the oral cavity around the dental treatment area.

In another type of embodiment (see EP 109 507), the preference is for a capacious seating on the side of the bur which allows the introduction, from the top, of a generously proportioned insert similarly affording ducts for the passage of the fluids and associated with seals for assembly of the head as a whole. Here too, the same drawbacks are encountered as described above, and in addition the insert has to be fashioned separately from the head through to the final configuration, with all the attendant consequences deriving from the need for precision fits between corresponding diameters (down to some few tenths of one millimeter).

What is more, in both the embodiments mentioned, the part of the spray circuit encompassed by the insert-and-head assembly is relatively consistent in volume, and water can therefore stagnate in the head during the pauses when the handpiece is not in use. Again, in these conventional embodiments, the passages afforded by the insert are positioned in a variety of circumferential arrangements designed to obtain a spray converging on the tip of the bur, and while this ensures that the treatment area and the tip are kept clean, it does not always favor or afford good lateral vision to the operator of the handpiece.

Moreover, the insert will not always be positioned faultlessly following assembly, and in particular, a lack of coaxial alignment between corresponding air and water passages can result in the correct operating conditions being impaired.

Accordingly, the object of the present invention is to overcome the aforementioned drawbacks through the adoption of a head for dentistry handpieces in which the geometry of the internal air and water passages is such as to ensure a safe and hygienic spray, affording optimum vision for the operator of the handpiece, and in which a more practical and superior level of design is achieved.

SUMMARY of the INVENTION

The stated object is achieved in a tool head of a turbine handpiece according to the invention, which affords an internal annular seating extending from the base of the turbine housing and connected to a fluid supply line; this same annular seating serves to accommodate a ring, affording a cavity connected by way of a lateral hole to a further fluid supply line, of which a portion not occupied by the cavity is embodied in such a way as to fill the annular seating only in part, leaving a gap at bottom to which fluid is admitted from the relative supply line. The ring in its turn affords a plurality of through holes connecting the cavity with the gap, and with a corresponding plurality of angled second holes formed in the bottom part of the head from which jets of mixed air and water are directed convergently at the tip of a tool fitted to the head.

One of the advantages afforded by the invention is that by incorporating the outlets of the spray circuit directly into the head, it becomes possible to reduce the axial proportions of the head and thus improve the maneuverability of the handpiece as a whole in operation.

BRIEF DESCRIPTION of the DRAWINGS

The invention will now be described in detail, by way of example, with the aid of the accompanying drawings, in which:

FIG. 1 illustrates a head according to the present invention, seen in plan from beneath;

FIG. 2 shows the head of FIG. 1, viewed in section through II—II.

DESCRIPTION of the PREFERRED EMBODIMENTS

As illustrated in the drawings, the head disclosed is designed for association with an instrument or handpiece as used in dentistry; such a handpiece comprises a grip 1 of which one end is connected with a head 2 for the support and retention of a rotary cutting or grinding tool 3 (for example a conventional bur, represented by phantom lines in FIG. 2), and the remaining end with pipelines 4, 4a and 5 supplying pressurized fluids, respectively air and water.

The three fluid supply lines are extended through the grip 1 up to the head 2, where air is directed from the line denoted 4a (shown in part only, not being essential to the invention) onto a turbine 3a (also conventional and represented by phantom lines in FIG. 2) accommodated internally of a relative housing 6 and serving to set the bur 3 in rotation; the remaining lines 4 and 5 supply air and water, mixed, to a set of spray outlet ducts 7 converging on the tip of the bur 3.

8 denotes an annular seating formed internally of the head 2, compassing and adjacent to the bottom of the housing 6 occupied by the turbine 3a, which is connected at bottom with the line denoted 5 in FIG. 2, that is, the line carrying water. 9 denotes a first ring occupying a stable position internally of the annular seating 8 and affording a cavity 10 connected by way of a lateral hole 11 with the remaining air line 4; a portion of the ring 9 not occupied by the cavity 10 is of shape such that it fills the annular seating 8 only in part, thereby creating a gap 12 at the bottom of the seating into which water is admitted from the relative line 5.

The part of the first ring 9 not occupied by the cavity 10 affords a plurality of through holes 7a by which the cavity 10 is connected to the gap 12 and also to a corresponding plurality of second holes 7b, coinciding with the aforementioned outlet ducts 7; these second holes 7b are formed in the lower part of the head 2 and set at an angle in relation to the longitudinal axis X of the bur 3 (the preferred angle for each hole is 23°), in such a way that the emerging spray of air and water can be directed substantially at the tip of the bur 3.

In the embodiment illustrated by way of example (see FIG. 1 in particular), the bottom of the head 2 affords four circumferentially distributed second holes 7b which are disposed symmetrically on either side of the longitudinal axis Y of the handpiece, each at an angle of 30° from this same axis. 15 denotes a second ring (FIG. 2) insertable into the annular seating 8 from the exposed side and serving to enclose the seating 8 and the cavity 10 of the first ring 9 in a fluid-tight fit.

The method of embodying a tool head according to the invention comprises an initial construction step from which the head 2 emerges not only with the housing 6 to accommodate the turbine 3a, but also with the base of the housing extended downward to form a substantially annular seating 8 of which the bottom part is enclosed and connects with the water line 5 of the spray circuit.

Thereafter, the first ring 9 is inserted forcibly into the annular seating 8 in such a manner that the cavity 10 lies facing upwards and exposed, the lateral hole 11 is positioned in alignment with the air line 4 of the spray circuit, and the bottom part of the profile is separated from the seating 8 to create the gap 12 admitting water. The annular seating 8 and the cavity 10 are then capped tightly from above by inserting the second ring 15.

The next step is to form a first set of holes 7a disposed at an angle in relation to the axis X of the bur 3, an operation effected by penetrating the bottom of the head 2 from the exterior, continuing across the gap 12 into the corresponding part of the first ring 9 and through to the cavity 10; this allows fluids from the two connected supply lines 4 and 5 to emerge from the head.

The final step is to form a second set of holes 7b in the bottom part of the head 2, by boring out the corresponding part of the first holes 7a coaxially to a larger diameter.

A head fashioned in this manner thus permits of reducing the axial dimensions of the handpiece as a whole, and affords greater scope for proportioning the spray passages differently and selecting the quantities of fluids used in operation. The manner in which the outlet ducts are positioned affords improved lateral visibility to the operator of the handpiece. Moreover, the entire process of making the head is rendered faster and more precise than hitherto, especially as regards the connections between the various internal passages.

What is claimed

1. A tool head, in particular for instruments or handpieces used in dental surgery, comprising:

a turbine housing connected to one of a plurality of fluid supply lines entering the handpiece at one end and directed through the grip of the handpiece to emerge at the opposite, or head end, where air is directed from one line onto the turbine to set the tool in rotation, and air and water from the remaining lines are mixed together and directed through a plurality of outlet ducts converging on the tip of the tool;

an internal annular seating, located directly adjacent to and substantially compassing the base of the housing occupied by the turbine, of which the bottom is enclosed and connected to one of the fluid supply lines;

a first ring stably insertable in the annular seating, affording a cavity connected by way of a lateral hole to another of the fluid supply lines, an annular portion not occupied by the cavity, shaped in such a way as to fill the annular seating only in part and thus create a gap beneath the ring positioned to admit fluid from the relative supply line, and a plurality of holes by which the cavity is connected with the gap and with a corresponding plurality of second holes formed in the bottom part of the head, which coincide with the plurality of outlet ducts and are angled in relation to the longitudinal axis of the tool in such a way as to direct streams of mixed air and water convergently onto the tip of the tool;

a second ring, insertable into the open top of the annular seating in such a manner as to enclose the seating and the cavity of the first ring to a fluid-tight fit.

2. A head as in claim 1, wherein the second holes are at least two in number and occupy diametrically opposed positions on the bottom part of the head.

3. A head as in claim 1, wherein the second holes are four in number, occupying points on a common circumference of the bottom part of the head and symmetrically disposed, each displaced through 30° from the longitudinal axis of the handpiece.

4. A head as in claim 1, wherein each of the second holes is set at an angle of 23° in relation to the longitudinal axis of the tool.

5. A method of embodying a tool head in particular for handpieces used in dental surgery, having a grip of which one end carries the head, serving to support and retain a tool, and the remaining end connects with fluid lines respectively supplying power air, spray air and water, which are extended through the full length of the grip to emerge at the head where air from the power line is directed into a housing afforded by the head, accommodating a turbine by which the tool is set in rotation, and air and water from the remaining lines are mixed together and directed through a plurality of outlet ducts converging on the tip of the tool, comprising the steps of:

initially constructing a head affording the housing to accommodate the turbine, and with the base of the housing extended downward to form an annular seating of which the bottom part is enclosed and connected with a first spray fluid supply line;

forcibly inserting a first ring into the annular seating, of which one side affords an open cavity connected laterally by way of a through hole with a second spray fluid supply line, and the remaining side consists in an annular projection occupying only a part of the annular seating, thus creating a gap to which fluid is admitted from the first fluid supply line;

enclosing the annular seating and the open cavity by means of a second ring inserted from above to a fluid-tight fit;

forming at least a first set of through holes disposed at an angle in relation to the axis of the tool, by penetrating the bottom part of the head from the exterior, passing thence across the gap and through the annular projection of the first ring, in order to allow the egress of fluids from the connected supply lines.

6. A method as in claim 5, comprising the further step of enlarging the first holes in part so as to form a second set of holes coaxial with and of greater diameter than the first and passing through the bottom part of the head only.

* * * * *